(12) United States Patent
Kiehne (10) Patent No.: US 6,994,690 B2
(45) Date of Patent: Feb. 7, 2006

(54) SINGLE USE SYRINGE (75) Inventor: Bruce Leigh Kiehne, Slacks Creek (AU)

(73) Assignee: Occupational & Medical Innovations LTD, (AU)

( * ) Notice: Subject to any disclaimer, the term of this patent is extended or adjusted under 35 U.S.C. 154(b) by 8 days.

(21) Appl. No.: 10/181,950

(22) PCT Filed: Feb. 22, 2001

(86) PCT No.: PCT/AU01/00183

§ 371 (c)(1),
(2), (4) Date: Aug. 2, 2002

(87) PCT Pub. No.: WO01/62320

PCT Pub. Date: Aug. 30, 2001

(65) Prior Publication Data
US 2002/0193736 A1 Dec. 19, 2002

(30) Foreign Application Priority Data
Feb. 22, 2000 (AU) .................... PQ7688
May 22, 2000 (AU) .................. 36357/00

(51) Int. Cl.
A61M 5/00 (2006.01)
A61M 5/32 (2006.01)
A61M 5/31 (2006.01)
(52) U.S. Cl. .................... 604/110; 604/195; 604/240
(58) Field of Classification Search ........... 604/110, 604/192, 194, 195, 198, 240, 187; 128/919
See application file for complete search history.

(56) References Cited

U.S. PATENT DOCUMENTS

| 4,955,870 A | * | 9/1990 | Ridderheim et al. ........ 604/195 |
| 4,994,034 A | | 2/1991 | Botich et al. |
| 5,049,133 A | * | 9/1991 | Villen Pascual ............ 604/110 |
| 5,053,010 A | * | 10/1991 | McGary et al. ............. 604/110 |
| 5,125,898 A | * | 6/1992 | Kaufhold et al. ........... 604/110 |
| 5,180,369 A | * | 1/1993 | Dysarz ....................... 604/110 |
| 5,180,370 A | | 1/1993 | Gillespie |
| 5,201,710 A | | 4/1993 | Caselli |
| 5,211,629 A | | 5/1993 | Pressly et al. |
| 5,385,551 A | * | 1/1995 | Shaw .......................... 604/110 |
| 5,407,436 A | * | 4/1995 | Toft et al. ................... 604/195 |

(Continued)

FOREIGN PATENT DOCUMENTS

| EP | 609 167 | 8/1994 |
| WO | US98/07361 | 4/1998 |
| WO | 98/48869 | 11/1998 |

Primary Examiner—Nicholas D. Lucchesi
Assistant Examiner—Catherine S. Williams
(74) Attorney, Agent, or Firm—Hoffman Wasson & Gitler (57) ABSTRACT A single use syringe has a needle which is biased back into the barrel but which is prevented from doing so by a holding means which has an outer part and an inner part which are connected together by a frangible portion. The needle is held by the inner part. When the plunger is pushed towards the front of the barrel, it contacts the outer part and pushes it forwardly which stretches the frangible portion until it bursts. When the frangible portion breaks, the inner portion containing the needle is released and can shoot back into a hollow portion in the plunger through the frangible portion of the plunger head.

8 Claims, 7 Drawing Sheets

U.S. PATENT DOCUMENTS 5,843,034 A    12/1998  Redfern et al.
5,935,104 A *   8/1999  Janek et al. ................ 604/110
6,010,486 A     1/2000  Carter et al.
6,099,500 A     8/2000  Dysarz

* cited by examiner

SINGLE USE SYRINGE

FIELD OF THE INVENTION

This invention relates to a single use single use syringe and particularly relates to a single use syringe where the syringe needle is biased into the syringe body after use.

BACKGROUND ART

Single use syringes are required to reduce the risk of infection caused by needle sharing. Many types of single use syringes are known.

A disadvantage with most of these known syringes is the complexity of manufacture and the rather large number of parts which are required in order to allow the syringe to be used effectively.

This invention is directed to a single use syringe of the type which has a needle which can be shot into a hollow plunger stem upon completion of the plunger stroke to prevent the needle from being use again. In particular, the invention is directed to a relatively simply insert which is fitted into the needle and which can securely hold the needle in its use position but which can release the needle to shoot the needle back into the plunger stem.

These types of syringes are known. One type of syringe which shoots the needle back into the syringe body is extremely complicated and has up to 16 parts which must be assembled to form the finished syringe. Some of the parts need to be glued as the parts are too small for injection or die moulding. This known syringe is also restricted to volumes of larger than 3 ml as the various parts cannot be made to fit smaller syringes.

Another disadvantage with known syringes of this type is the inability to easily and readily injection mould the various components. For instance, a syringe having a shoot back needle is known where a spring biased needle is held in place by a rupturable restraining means which is moulded as part of the internal wall of the syringe barrel. In practice, it is found that such a barrel is extremely difficult to mould and is virtually impossible to injection mould. Thus, this type of syringe cannot be manufactured cheaply.

Another type of safety syringe having a spring mounted needle which shoots back into the plunger stem has a needle held in place by a deformable base. The deformable base has a constricted passageway which grips a peculiarly designed needle which has inter alia a circular flange attached to it. The deformable member is pushed forward by the plunger and in doing so, it is pushed forwardly into an area of larger cross-section which allows the deformable member to expand which in turn allows the needle to pass through the passageway in the deformable member and to shoot back into the plunger stem. It is believed that this type of arrangement would not be particularly reliable as it does not include a more reliable frangible portion which is broken to allow the spring biased needle to shoot back into the plunger stem.

Safety syringes having shoot back needles are also known where the needle is not biased by a spring. Instead, a vacuum is provided in the barrel to suck the needle back into the plunger stem. This type of syringe is of course fairly limited in use to circumstances where suction can be provided.

Another type of syringe has a plunger stem provided with a helical spring such that the plunger stem is biased to retract. The plunger stem is pushed along the barrel and against the bias of the spring. When the front of the plunger stem strikes the rear of the needle, it locks against the needle. Release of the plunger stem will then cause the spring to pull the plunger stem back along the barrel thereby retracting the needle.

It is known to provide single use syringes where the needle is spring biased and is held in place by a cuttable member. In order to ensure that the member is properly cut thereby releasing the needle, a two-part cutting action is usually required. In the two-part cutting action, the plunger typically has a forward cutting edge and the front of the needle also has some form of cutting edge and a double cutting action is required to ensure that the cuttable member is properly cut to release the needle. It is found that attempting to cut a cuttable member to release a spring biased needle is not always reliable and does not always work.

Another type of known single use syringe has a base member which grips an enlargment on the needle. The plunger pushes the base member forwardly which further compresses a spring which is around the needle. The pushing action releases the grip between the base member and the enlargement on the needle. This allows the needle containing the enlargement to be shot back into the plunger while leaving the spring behind. The spring is initially compressed partially but then becomes compressed fully as the plunger forces the base member forwardly. This arrangement requires a needle having a special design (containing an enlargement) which means that conventional needles cannot be used.

Another type of syringe has a plunger seal which moves on the plunger and where the plunger seal slides rearwardly along a bearing surface in response to a force being applied to the seal which is in excess of the operational force of the syringe. This arrangement begins the retraction sequence of the needle. With this arrangement, a specially designed plunger seal is required which moves relative to the plunger. Conventional plungers have a plunger seal which is fixed to the plunger.

Another type of syringe has a shoot back arrangement which consists of two parts which slide relative to each other to release the needle. The two parts consist of an outer part and an inner part. The inner part holds the needle and is biased by a helical spring. The two parts are held together by frictional engagement to each other. A plunger progressively pushes the outer part forwardly thereby progressively reducing the amount of frictional engagement between the outer part and the inner part until such time that the bias of the spring is sufficient to shoot the inner part away from frictional engagement with the outer part. This arrangement requires a sliding frictional grip to hold the two-part together which is considered quite risky and requires careful manufacture.

Another arrangement uses a needle holder having an elongate body portion in front and a head end in back and providing a spring under the head end which circumscribes the needle holder. The use of an elongate body in a needle holder makes this arrangement difficult for use small and confined spaces.

OBJECT OF THE INVENTION

The present invention is directed to a single use syringe having a spring biased needle which can shoot back into a hollow plunger stem after use. The needle is held in place against the bias of the spring by a particularly designed holding means. The holding means has a frangible portion which can be broken to release the needle and to allow the needle to shoot back into the plunger stem. In this invention, the frangible portion is broken by a stretching action which bursts the frangible member rather than a cutting action which is found to be much less reliable. The holder can be formed separately and inserted into the syringe thereby doing away with the requirement for complicated or difficult to mould integral portions. This also allows much of the syringe to be formed of conventional inexpensive components or from components which require only minor modification and which can be made inexpensively especially by injection moulding.

Thus, one form of the invention has a syringe having relatively few parts being a plunger, a barrel, a needle attached to a needle holder, and a particularly designed holding means having a frangible portion which can be stretched to breaking point to release the needle.

It is an object of the invention to provide a single use syringe which may overcome the abovementioned disadvantages or provide the public with a useful or commercial choice.

In one form, the invention resides in a syringe body comprising a barrel,
(a) a plunger slideable in the barrel, the plunger having a plunger head and an elongate stem, the stem having an extending longitudinal passageway which has an open end which is sealed by frangible portion on the plunger head,
(b) a hollow needle,
(c) biasing means about the needle to bias the needle into the barrel,
(d) holding means which is formed separately from the barrel and which is positioned inside a forward portion of the syringe and which holds the needle against movement into the barrel, the holding means having a first part which is able to be pushed forwardly by the plunger, a second stationary part to which the needle is attached, and,
(e) a frangible portion interconnecting the first and second parts and which is broken when the first part is pushed forwardly to allow the biasing means to bias the needle into the longitudinal passageway in the stem.

Preferably, the first part is an outer body of the holding means.

Preferably, the second part is an inner member of the holding means.

The hollow needle may have an internal end which is associated with an extension which passes into the barrel and which can weaken or pierce the frangible portion on the plunger head to facilitate passage of the needle into the plunger stem. The extension may form part of the holding means.

In another form, the invention resides in a holding means for holding a medical needle, the holding means having a first part in the form of an outer cylindrical body, a second part in the form of an inner member, the first part and the second part being interconnected by a frangible portion, the inner part having a passageway to fit the end of the needle.

Preferably, the longitudinal passageway in the stem is tapered to grip and hold the needle in the passageway.

The single use syringe has a hollow needle which is biased to shoot into the passageway in the plunger stem, but where the needle is held back by a holding means. The holding means has a weak, frangible, pierceable, or other type of breakable portion which, when broken, will cause the needle to shoot into the plunger stem.

The frangible portion can be broken by a means on the plunger (typically adjacent a forwardmost portion of the plunger) such that as the plunger is pushed towards the end of the barrel, it will stretch and break the frangible portion to cause the needle to shoot into the plunger stem.

The plunger has a plunger head, a portion of which can be pierced by the needle or extension. This portion can be a frangible portion or a relatively thin portion on the plunger head.

Thus, as the plunger is pushed towards the end of the barrel, the extension on the needle can contact the frangible portion on the plunger head at about the same time that the means on the plunger begins to stretch the frangible portion on the holding means. Firmly pushing the plunger against the end of the barrel can cause the needle or extension to pierce through the frangible portion on the plunger head as well as causing the needle to become free to allow it to shoot into the hollow plunger stem.

The syringe body has a barrel which is typically cylindrical and which can be of various diameters and lengths depending on the volume of liquid to be held by the syringe. Typical volumes would be from between 1 to 10 mm although larger and smaller volumes are envisaged.

A plunger is provided which slides in the barrel. The plunger has an elongate stem which can be formed from plastics material. The inner end of the stem has a plunger head which is usually formed of black resilient material such as rubber, silicone, and the like.

The plunger head, or plunger bung comprises a relatively thin portion (which can be called a membrane) which deforms and ultimately ruptures as the plunger is pushed against a forward part of the syringe. It is preferred that membrane is allowed to be form or stretch to substantially conform to the forward part of the syringe against which the membrane is pushed, prior to the membrane rupturing. The advantage is that virtually all the fluid in the syringe will be expelled through the needle and there will be little or no residual fluid left between the plunger head and the forward part of the syringe.

The stem has an extending longitudinal passageway which has an open end which is sealed by a thin or frangible portion or membrane which forms part of the plunger head. The internal passageway may extend entirely along the plunger stem and it is preferred that the passageway narrows towards the end of the plunger stem for reasons which will be described in greater detail below.

As the longitudinal passage functions to hold the used needle, it is envisaged that there may exist other combinations or configurations which may do a similar function. For instance, the plunger stem, instead of having a hollow passageway, may be provided with a longitudinal groove or slot which can have means to hold the needle. The internal wall of the barrel may function in cooperation with the plunger stem to define part or all of the longitudinal passageway in which the needle passes. However, it is preferred that the stem itself is substantially hollow to define the longitudinal passageway.

The wall of the hollow passageway may have a necked area which contains at least one opening. The shot back needle assembly may have an edge which deforms as the needle assembly shoots back through the stem but which can expand into the opening to lock the needle assembly to the stem. This can prevent the needle assembly from being easily removed or from falling accidentally out of the stem and presenting a sharps hazard.

The syringe has a hollow needle. The hollow needle is attached to the holding means. The holding means may be provided with an extension which extends into the barrel to assist in stretching and rupturing the frangible portion on the plunger head.

A biasing means is provided to bias the needle into the barrel. The biasing means may comprise a spring which may extend about the needle body and which may be compressed when the needle is fitted to the syringe such that the needle is naturally biased to shoot into the longitudinal passage. The spring may extend at least partially about the holding means which is described below.

A holding means is provided. The holding means may be in the form of a small plastic or other member. The holding means is attached to the syringe and is preferably attached adjacent the inner end of the needle. The holding means can grip the needle to prevent the needle from shooting into the longitudinal passage under the influence of the biasing means. The holding means has a frangible, breakable, pierceable, or other type of arrangement which can be broken or removed to release the needle such that it can pass into the longitudinal passageway under the bias of the biasing means. The frangible portion may be in the form of an area of reduced thickness on the holding means.

The holding means comprises a first part which is able to be pushed forwardly by the plunger and a second part to which the needle is attached and which typically does not move relative to the first part. The first part may comprise an outer body and the second part may comprise an inner member. The frangible portion can interconnect the first and second parts and is designed such that when the first part is pushed forwardly relative to the second part, the frangible portion is stretched to breaking point.

The frangible portion may be formed integrally with the first part and the second part. The frangible portion may have an upper breakthrough edge and a lower breakthrough edge. The upper breakthrough edge typically faces the plunger while the lower breakthrough edge typically faces the spring. The upper breakthrough edge may comprise an annular groove or recess of smaller size and the lower breakthrough edge may comprise an annular groove or recess of larger size. The upper breakthrough edge is preferably located on the outside of the lower breakthrough edge when viewed in section.

A means may be provided which can be on the plunger to break the frangible portion of the holding means to release the needle.

BRIEF DESCRIPTION OF THE DRAWINGS

Embodiments of the invention will be described with reference to the following drawings in which.

DETAILED DESCRIPTION

Figure 1:
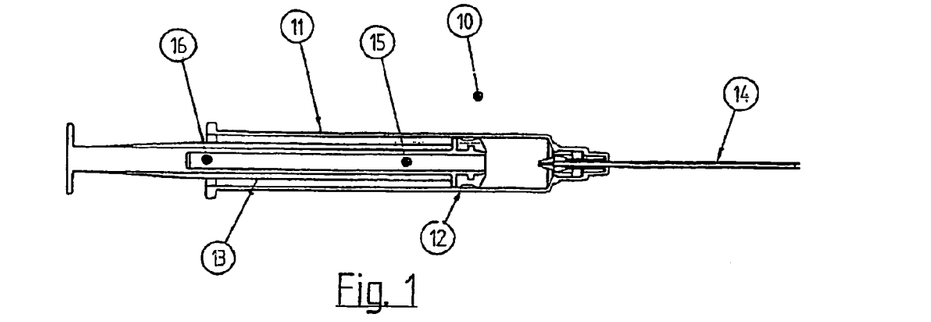
FIG. 1 is a view of a single use syringe according to an embodiment of the invention.

Referring to the drawings and initially to FIG. 1, there is illustrated a single use syringe 10, which like other syringes has a barrel 11, a slidable plunger which is formed from a plunger head 12 and plunger stem 13, and a hollow needle 14.

Figure 2:
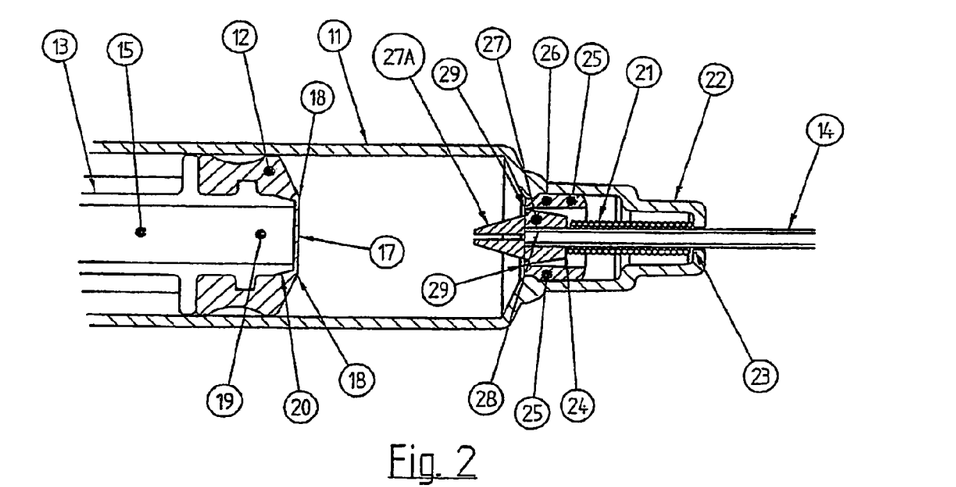
FIG. 2 is an enlarged view of the forward end of the syringe showing the plunger being pushed towards the end of the barrel.

FIG. 2 illustrates the forward part of the syringe in greater detail. The elongate plunger stem 13 is hollow to define an internal longitudinal passageway 15 with the end 10 (see FIG. 1) of the passageway 15 being tapered for reasons which will be described in greater detail below.

The front of passageway 15 is capped or sealed by a frangible portion 17 of plunger head 12. Portion 17 is frangible in the sense that there exists a thin-walled portion 18 which can be perforated. This portion can also be seen as a membrane. Stem 13 has at forward area 19 to which plunger head 12 is fitted. Forward area 19 has an annular leading edge 20 which in the embodiment functions as a means to break the frangible portion.

Needle 14 is biased by a biasing means in the form of a helical spring 21 extending about the needle body, the spring being positioned in the nipple area 22 of the syringe. Spring 21 has one end 23 abutting against an internal wall of nipple area 22, and has another end 24 pushing against the back of a holding means.

Needle 14 is held in place by a holding means in the form of a resilient cap 26 or holding means. Cap 26 has an annular outer body 25 which can slide forwardly along a formed recess 22A (see FIGS. 5 to 8) in the nipple area 22 of the syringe. Cap 26 has a second part in the form of an inner sacrificial member 27 formed with a tubular passageway which grips against the outside of the internal end 28 of needle 14.

Sacrificial member 27 is separated from body 25 by a thin walled annular frangible portion 29. Sacrificial member 27 has an extension 27A which is cone-shaped and which extends into the barrel. Extension 27A has a longitudinal bore 27B which communicates with the needle to allow the contents of the barrel to pass through bore 27B and through the needle.

Figure 3:
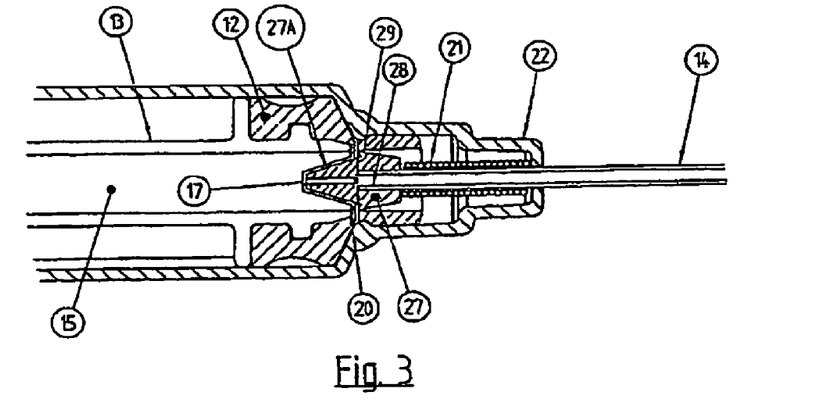
FIG. 3 illustrates the forward end of the syringe where the plunger barrel is about to break the frangible portion on the holding means and the internal end of the needle is about to break the frangible portion on the plunger head.

Referring to FIG. 3, in this figure, the plunger head 12 is being pushed against the end of the barrel. The extension 27A is pushing against, and is inwardly deflecting the frangible portion 17 on the plunger head. At this point, the annular edge 20 of plunger stem 13 is pushing against the annular outer body 25. Continued pushing will result in annular edge 20 pushing the outer annular body 25 away from the sacrificial member 27 thereby stretching the frangible portion to bursting point, while at the same time, the sacrificial member 27 and the internal end of needle 14 pierces through frangible portion 17 on the plunger head. This is illustrated progressively in FIGS. 5 to 8.

Figure 5:
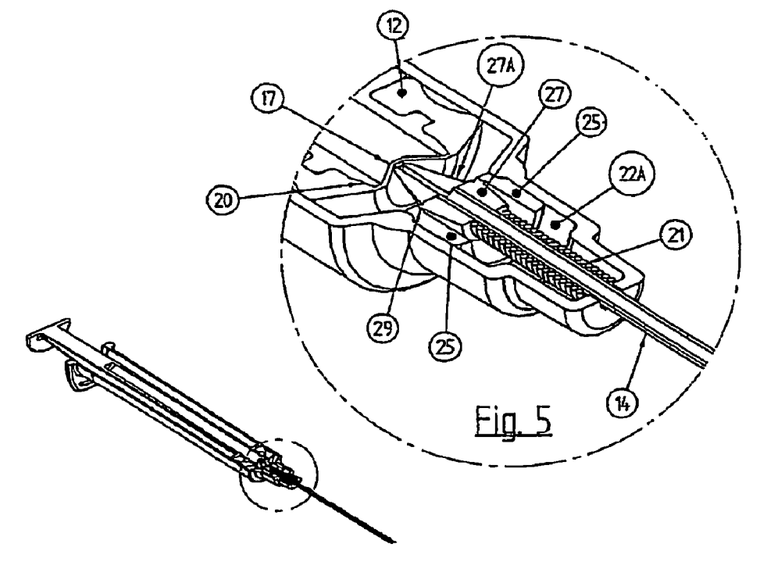
FIGS. 5, 6, 7 and 8 illustrate progressively the action by which the frangible portion is stretched and broken to allow the spring biased needle to shoot into the plunger stem.
Figure 6:
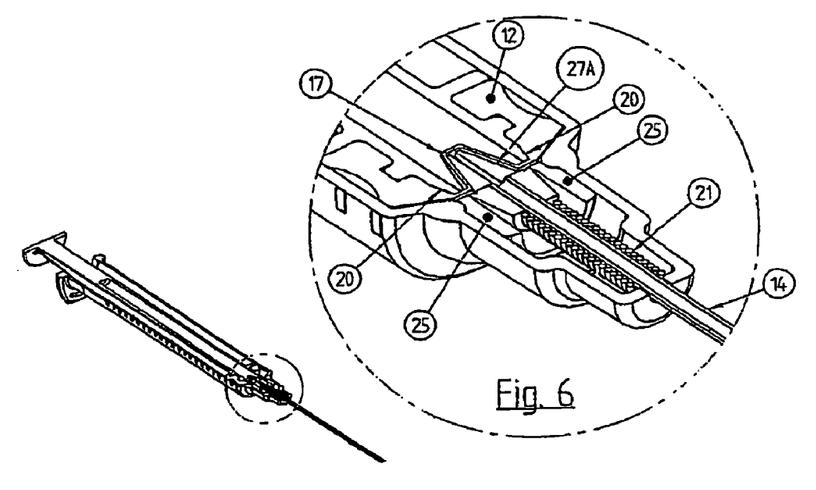
Figure 7:
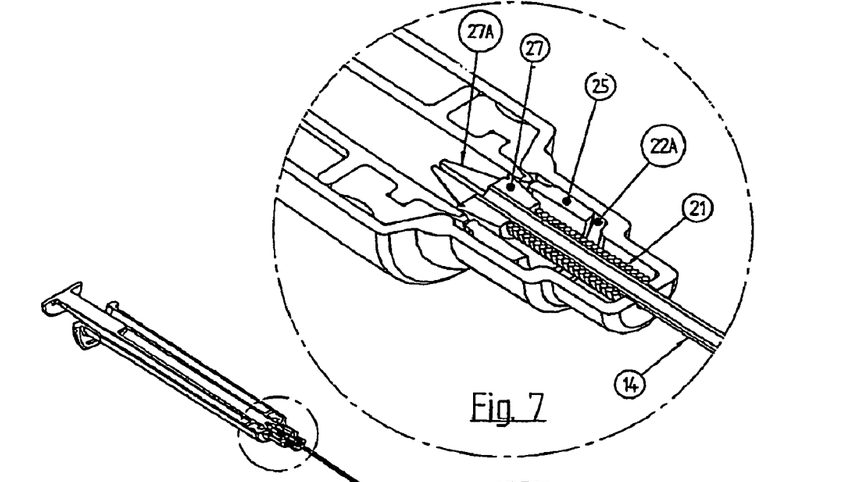
Figure 8:
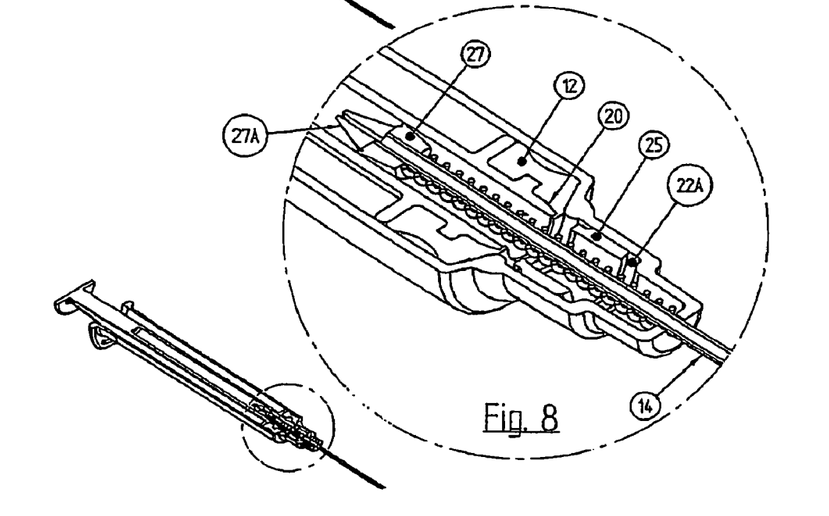

In FIG. 5, the plunger head is just contacting extension 27A. In FIG. 6, the annular edge 20 of the plunger is abutting against an edge of outer annular body 25 but has not yet begun to push the outer annular body forwardly. In FIG. 7, further pushing of the plunger stem now causes the outer annular body 25 to be pushed forwardly along the formed recess 22A. At the same time, the inner sacrificial member 27 is unable to move forwardly as it abuts against the compressed helical spring around the needle also the mating faces of the tip and the body boss. FIG. 7 illustrates the position where the frangible portion 17 is stretched to bursting point. In FIG. 8, the frangible portion has been burst which now allows the spring to expand to shoot the needle back into the plunger stem. The needle is still fixed to the inner sacrificial member 27.

Figure 4:
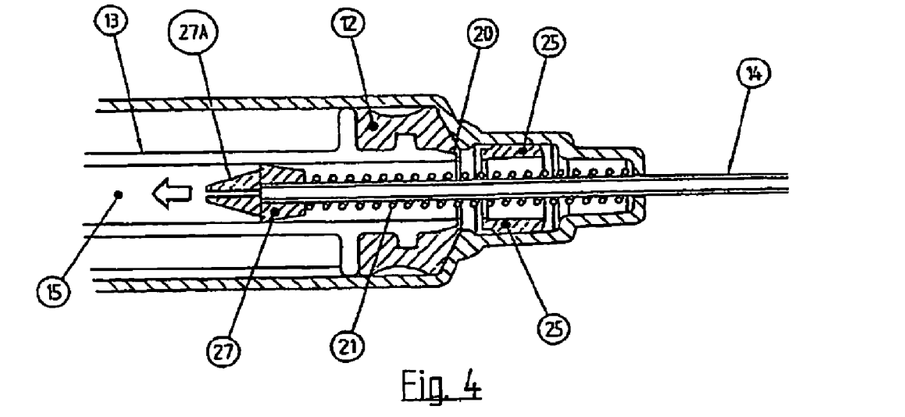
FIG. 4 shows the release position where the needle has been released from the holding means and has been shot into the longitudinal passageway of the plunger stem under the influence of the biasing means.

Referring to FIG. 4, the sacrificial member 27 which grips needle 14 has been released from the main body 25 of cap 26 and spring 21 expands to shoot needle 14 along the hollow longitudinal passageway 15 in the plunger stem 13. The force of the spring is typically sufficient to shoot the needle entirely along the passageway until sacrificial member 27 becomes wedged in the tapered portion 16 in passageway 15 (FIG. 1 illustrates the tapered portion). The needle is now held securely in the passageway and will not fall out should the plunger be removed from the barrel.

The sacrificial member 27 has at least one opening in it which communicates with an opening in the needlestick wall such that when the plunger is in the position approximating that of FIG. 3, (when the end of the needle is sealed by the plunger head), the last bit of liquid in the barrel can pass through the needle.

Figure 9A:
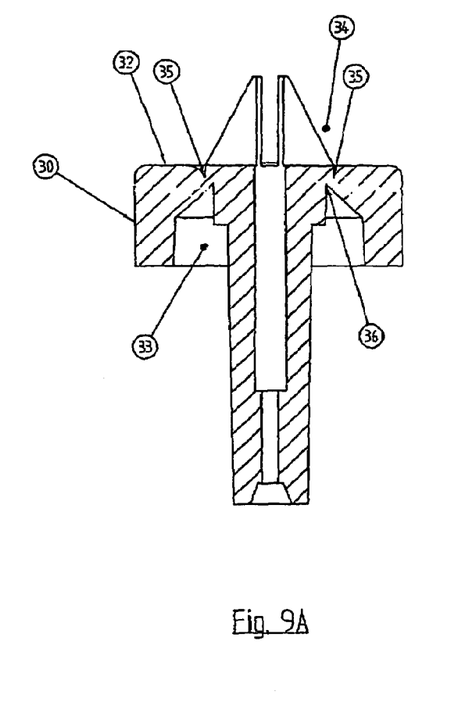
FIGS. 9A and 9B illustrate, in cross-section, a particularly preferred type of holding means having an upper breakthrough edge and a lower breakthrough edge.
Figure 9B:
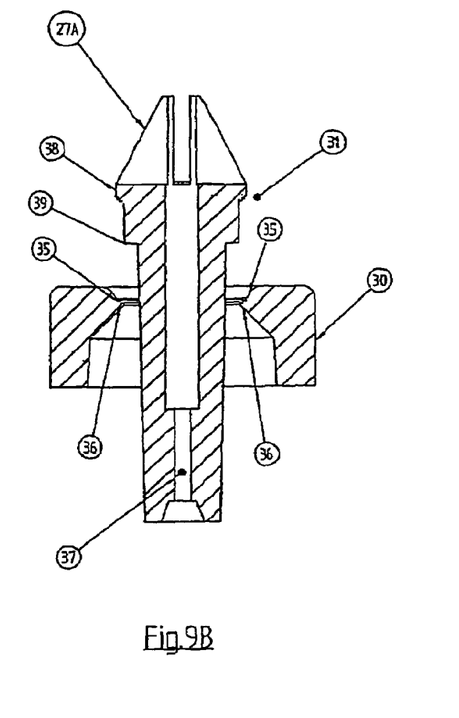

Referring to FIGS. 9A–9B, there is illustrated a holding means according to an alternative embodiment. The holding means is formed from a single piece of material and comprises an outer part 30 and an inner part 31. Outer part 30 is cylindrical in configuration, has a substantially solid upper wall 32 (which faces the plunger) and a substantially hollow inner portion 33. Outer part 30 and inner part 31 are connected by an annular thin wall frangible section 34, the frangible section 34 comprises an upper breakthrough edge 35 and a lower breakthrough edge 36. Upper breakthrough edge 35 comprises an annular recess in the upper wall 32, while lower breakthrough edge 36 comprises an annular recess which is an extension of the hollow inner portion 33. Both breakthrough edges 35, 36 have an inner wall which is substantially parallel with the longitudinal axis of the syringe, and an outer wall which is inclined towards the inner wall to form a substantially triangular shaped recess. The breakthrough edges create the relatively thin frangible portion which connects the outer part 30 with the inner part 31. Upper breakthrough edge 35 is positioned to extend on the outside of the inner wall of lower breakthrough edge 36 (when viewed in section). This positioning facilitates a reliable stretching and bursting action of the frangible section 34. FIG. 9B illustrates the holding means after the frangible section has been burst.

Inner part 31 has a longitudinal passageway 37 through which the needle (not illustrated) passes. Inner part 31 has an extension 27A which is similar to that described in previous figures. In this particular embodiment, when the outer part 30 has been separated from the inner part 31, edges are formed 38, 39 which assist in a locking the shot back inner part into the plunger stem is will be described below.

Figure 10:
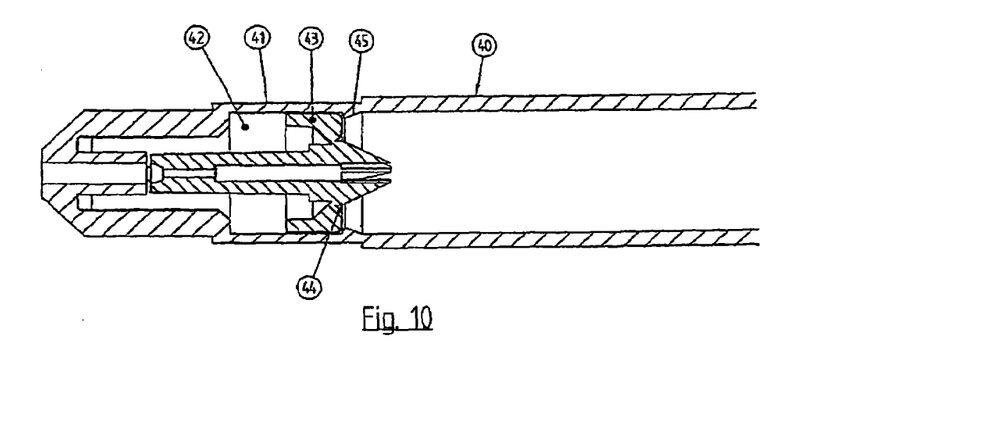
FIG. 10 illustrates an embodiment of the invention which provides a good secure fit of the holding means in the barrel.

Referring to FIG. 10, this figure illustrates an embodiment of the invention to securely hold or lock the tip portion into the syringe barrel. The syringe barrel 14 has a reduction in the wall thickness 41 in a forward part of the syringe barrel. The reduction in the wall thickness 41 makes this part of the barrel weaker and therefore able to deform or bulge when the holding means is pressed into this part of the syringe. This provides a very secure fit and aids in the creation of a fluid seal between the holding means and the barrel. This part 41 of the barrel has a passageway 42 along which outer part 30 of the holding means can slide when the outer part 30 is pushed by the plunger (not illustrated). By having the part of reduced wall thickness, the frictional force between part 30 and the inside wall of passageway 42 is reduced. This reduces the amount of forward pushing required on the plunger to push outer part 30 thereby bursting the frangible portion 44 as described above. The tip (or holding means) is secured in the syringe barrel by a one-way location/sealing ring 45 which is formed at the point of manufacture.

Figure 11A:
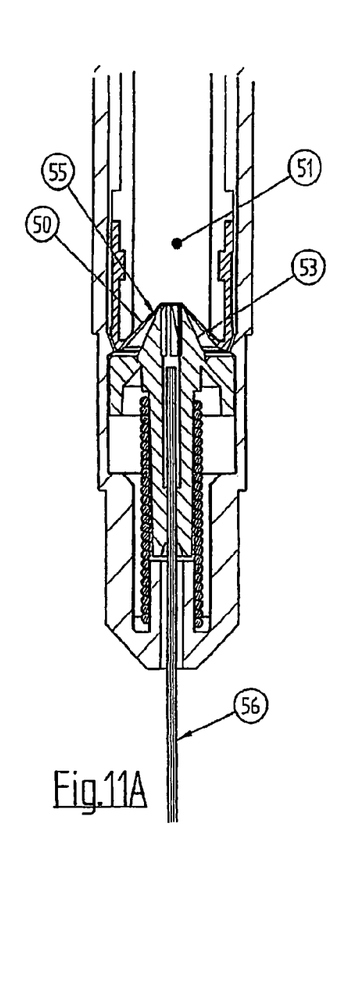
FIGS. 11A–11C illustrate sequentially deformation of the plunger tip or membrane and particularly illustrating the plunger tip conforming to the shape of the forward part of the syringe to expel all the fluid in the syringe.
Figure 11B:
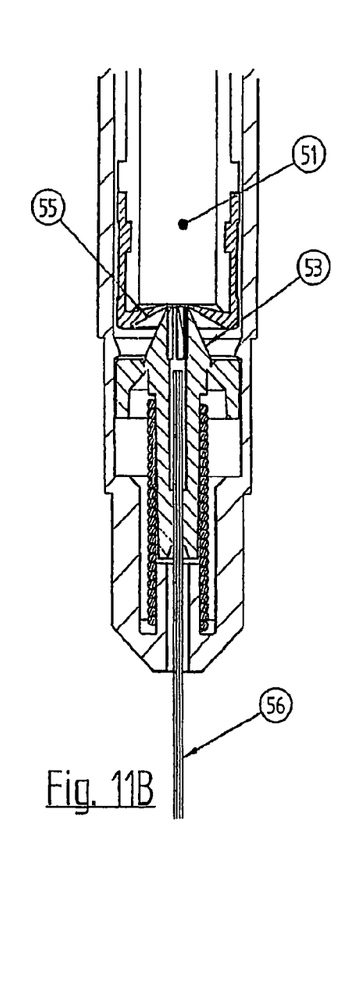
Figure 11C:
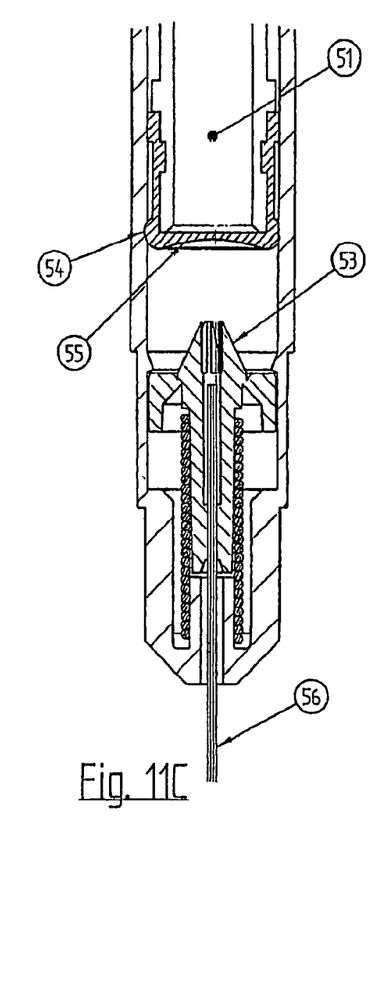

FIGS. 11A–C illustrate sequentially the deformation of the membrane 50 of the thin portion on the plunger. FIG. 11A shows plunger 51 approaching the end of syringe 52, this end containing the tip 53. Plunger 51 has a front seal 54 which has a thin membrane portion 55. FIG. 11B shows plunger 51 beginning to make contact with tip 53 and with membrane 55 beginning to deform inwardly. FIG. 11C shows plunger 51 being pushed hard up against tip 53 with membrane 55 being sufficiently pliable to conform to the shape of tip 53 thereby ensuring that there are no fluid containing voids between the membrane 55 and the outer face of tip 53. This ensures that virtually all the fluid in the syringe passes through the needle 56. The membrane 55 stretches until the plunger is fully depressed and substantially all the fluid is expelled from the syringe leaving no "dead space" or wasted fluid. At the point of full plunger depression, the elastic threshold of the membrane is overcome and the membrane ruptures to allow simultaneous movement of the inner part (spring-loaded) which contains the needle into the stem of the barrel (i.e. shooting back into the stem).

Figure 12A:
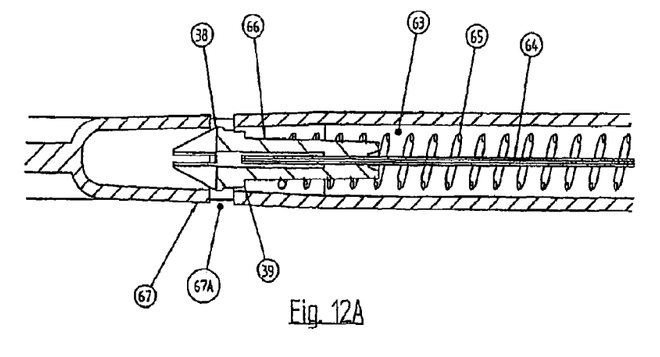
FIGS. 12A–12B illustrate an embodiment where the plunger stem is provided with a shoulder or stop to securely lock the shot back needle.
Figure 12B:
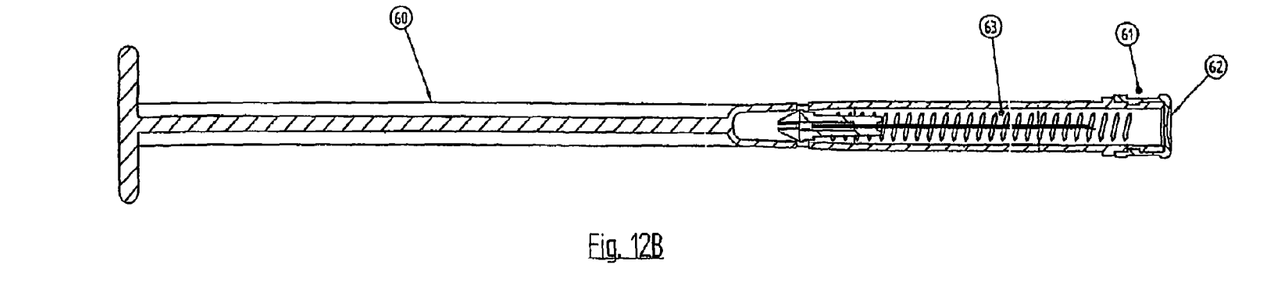

FIGS. 12A and 12B illustrates a stem design according to an embodiment of the invention. The stem forms part of the plunger and contains a main body portion 60 and a forward portion 61 which has the plunger seal 62. A hollow portion 63 is provided to accommodate the detached needle assembly. The detached needle assembly is as described above and contains the needle 64, the helical spring 65, and the inner part 66 of the holding means which has been detached from the outer part. Hollow portion 63 contains a necked area 67 which has at least one opening 67A to provide an unrestricted location and as illustrated in FIG. 12A. Inner part 66 can be as illustrated in FIG. 9B and has an edge 38 which deforms as the needle assembly shoots through the tapered plunger stem. When the needle assembly passes opening 67A, the deformed edge 38 can expand into the opening to lock the needle assembly to the stem.

The plunger stem can be provided with openings in the side wall to allow water to enter into the syringe after use which prevents the used syringe from floating on water dependent on material. This may reduce the number of used needles washed up on a sea shore.

The single use syringe uses relatively few parts and the parts can be assembled without the use of any adhesive. The arrangement works on a cutting and piercing action to release the needle once the plunger head is pushed against the end of the barrel.

It should be appreciated that various other changes or modifications can be made to the embodiment described without departing from the spirit and scope of the invention as claimed.

The invention claimed is:

1. A single use syringe comprising a barrel, and
   a. a plunger slideable in the barrel, the plunger having a plunger head and an elongate stem, the stem having an extending longitudinal passageway which has an open end which is sealed by frangible portion on the plunger head,
   b. a hollow needle,
   c. biasing means about the needle to bias the needle into the barrel,
   d. holding means which is formed separately from the barrel and which is positioned inside a forward portion of the syringe and which holds the needle against movement into the barrel, the holding means having a first part which is adapted to be pushed forwardly by the plunger, a second stationary part to which the needle is attached, and a frangible portion interconnecting the first and second parts and which is broken when the first part is pushed forwardly to allow the biasing means to bias the second part containing the attached needle through the plunger head and into the longitudinal passageway in the stem,
   e. said first part of said holding means comprises an outer part, and said second part of said holding means comprises an inner part,
   f. said inner part of said holding means has a front end and a rear end, the rear end communicating with the inside of said barrel, the rear end comprising a tapered extension which extends into the barrel and which is adopted for contact with the frangible portion on said plunger head,
   g. the frangible portion on said plunger head being broken by contact with the tapered extension as said plunger is pushed against said holding means, and
   h. wherein said frangible portion on said plunger head substantially conforms to the shape of the tapered extension prior to breaking to facilitate expulsion of all the liquid in the syringe.

2. The syringe of claim 1, wherein the longitudinal passageway in the stem is tapered to grip and hold the needle in the passageway.

3. The syringe of claim 2, wherein the longitudinal passageway is provided with at least one opening in the wall of the passageway, which is adapted to engage with the second part containing the needle when the second part is shot back into the passageway.

4. The syringe of claim 1, wherein the biasing means comprises a helical spring which is attached to the second part.

5. The syringe of claim 4, wherein the first part has a cylindrical outer face adapted for a sliding contact with a portion of the inner wall of the barrel.

6. The syringe of claim 5, wherein the portion of the inner wall of the barrel has a thickness which is less than the thickness of the wall of a main body.

7. The syringe of claim 1, wherein the holding means comprises a unitary member, and the frangible portion has an upper breakthrough edge which faces the plunger and a lower breakthrough edge, the edges comprising annular recesses in the holding means.

8. The syringe of claim 7, wherein the upper breakthrough edge is located on the outside of the lower breakthrough edge when viewed in section.

\* \* \* \* \*